United States Patent [19]

Naumann et al.

[11] 4,183,950
[45] Jan. 15, 1980

[54] COMBATING ARTHROPODS WITH 2,2-DIMETHYL-3-VINYL-CYCLOPROPANE CARBOXYLIC ACID ESTERS OF HALOGENATED BENZYL ALCOHOLS

[75] Inventors: Klaus Naumann, Cologne; Wolfgang Behrenz, Overath; Ingeborg Hammann, Cologne; Erich Klauke, Odenthal; Albrecht Marhold, Leverkusen, all of Fed. Rep. of Germany

[73] Assignee: Bayer Aktiengesellschaft, Leverkusen, Fed. Rep. of Germany

[21] Appl. No.: 844,852

[22] Filed: Oct. 25, 1977

[30] Foreign Application Priority Data

Dec. 22, 1976 [DE] Fed. Rep. of Germany ....... 2658074
Mar. 30, 1977 [DE] Fed. Rep. of Germany ....... 2714042

[51] Int. Cl.² .......................... C07C 69/74; A01N 9/30
[52] U.S. Cl. .................................. 424/305; 424/306; 560/124
[58] Field of Search .................. 560/124; 424/305, 306

[56] References Cited

U.S. PATENT DOCUMENTS

| 3,358,011 | 12/1967 | Elliott | 560/124 |
| 3,567,740 | 3/1971 | Matsui | 560/124 |
| 3,792,079 | 2/1974 | D'Orazio | 560/124 |
| 3,998,868 | 12/1976 | Mizutani | 560/124 |

FOREIGN PATENT DOCUMENTS

| 39-17182 | 8/1964 | Japan | 424/306 |
| 50-3370 | 4/1975 | Japan | 424/306 |
| 1401279 | 7/1975 | United Kingdom | 560/124 |
| 1413491 | 11/1975 | United Kingdom | 560/124 |
| 1438129 | 6/1976 | United Kingdom | 560/124 |

OTHER PUBLICATIONS

Elliott, Proceedings 7th British Insecticide & Fungicide Conference, pp. 721-728 (1973).
Elliott, Pestic. Sci., 6, pp. 537-542 (1975).
Elliott, Nature, 246, pp. 169-170 (1973).
Elliott, Bull. Wld., Hlth, Org., 44, pp. 315-324 (1970).

*Primary Examiner*—James O. Thomas, Jr.
*Assistant Examiner*—Michael Shippen
*Attorney, Agent, or Firm*—Sprung, Felfe, Horn, Lynch & Kramer

[57] ABSTRACT

2,2-Dimethyl-3-vinyl-cyclopropane carboxylic acid esters of halogenated benzyl alcohols of the formula

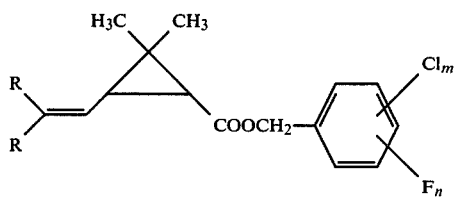

in which
each R independently represents F, Cl, Br or $CH_3$ and m and n each represent 0, 1, 2, 3, 4 or 5 subject to the sum of m+n being not more than 5, with the provisos that
(i) when each R represents F or Br then m and n cannot both be 0,
(ii) when each R represents Cl, then m represents 0, 1, 2, 3 or 4 and n represents 1, 2, 3, 4 or 5, and
(iii) when each R represents $CH_3$, then m represents 0 and n represents 5, which possess arthropodicidal properties.

9 Claims, No Drawings

COMBATING ARTHROPODS WITH 2,2-DIMETHYL-3-VINYL-CYCLOPROPANE CARBOXYLIC ACID ESTERS OF HALOGENATED BENZYL ALCOHOLS

The present invention relates to and has for its objects the provision of particular new 2,2-dimethyl-3-vinyl-cyclopropane carboxylic acid esters of halogenated benzyl alcohols which possess arthropodicidal properties, active compositions in the form of mixtures of such compounds with solid and liquid dispersible carrier vehicles, and methods for producing such compounds and for using such compounds in a new way especially for combating pests, e.g. arthropods, with other and further objects becoming apparent from a study of the within specification and accompanying examples.

It has already been disclosed that esters of 2,2-dimethyl-3-(2-methylbuten-1-yl)-cyclopropanecarboxylic acid with polychlorinated benzyl alcohols exhibit insecticidal properties (French Pat. No. 2,271,196 and Japanese Patent Specification No. 75/003,370). These substances do not always have a satisfactory action in respect of speed, intensity and duration of action.

The present invention provides, as new compounds, the cyclopropanecarboxylic acid esters of halogenated benzyl alcohols, of the general formula

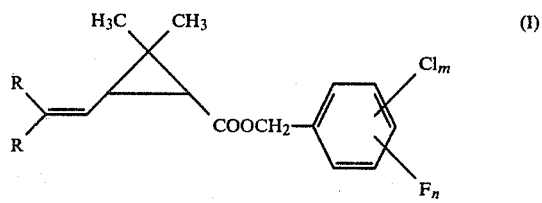

in which
each R independently represents F, Cl, Br or CH$_3$
and m and n each represent 0, 1, 2, 3, 4 or 5 subject to the sum of m+n being not more than 5,
with the provisos that
(i) when each R represents F or Br then m and n cannot both be 0,
(ii) when each R represents Cl, then m represents 0, 1, 2, 3 or 4 and n represents 1, 2, 3, 4 or 5, and
(iii) when each R represents CH$_3$, then m represents 0 and n represents 5.

Surprisingly, the esters according to the invention exhibit a strong and rapidly manifested insecticidal and acaricidal action. The said compounds therefore represent a valuable enrichment of the art.

Preferably, the R's, which may be identical or different, each represent F or Cl or Br (especially chlorine or bromine) while m represents an integer from 2 to 5 or n represents an integer from 3 to 5; or each R represents CH$_3$ while m represents 0 and n represents 5.

The following may be mentioned as examples of the active compounds according to the invention: 2,2-dimethyl-3-(2-methylbuten-1-yl)-cyclopropanecarboxylic acid pentafluorobenzyl ester, 2,2-dimethyl-3-difluorovinylcyclopropanecarboxylic acid pentafluorobenzyl ester, 2,2-dimethyl-3-dibromovinylcyclopropanecarboxylic acid pentafluorbenzyl ester, 2,2-dimethyl-2-dibromovinylcyclopropanecarboxylic acid pentachlorobenzyl ester, 2,2-dimethyl-3-dichlorovinyl-cyclopropanecarboxylic acid pentafluorobenzyl ester, 2,2-dimethyl-3-dichlorovinyl-cyclopropanecarboxylic acid 2,3,5,6-tetrafluorobenzyl ester, 2,2-dimethyl-3-dichlorovinylcyclopropanecarboxylic acid 2,4,6-trifluorobenzyl ester, 2,2-dimethyl-3-dichlorovinyl-cyclopropanecarboxylic acid 2,3,5-trifluorobenzyl ester, 2,2-dimethyl-3-dichlorovinyl-cyclopropanecarboxylic acid 2,4-difluorobenzyl ester, 2,2-dimethyl-3-dichlorovinyl-cyclopropanecarboxylic acid 2,6-difluorobenzyl ester, 2,2-dimethyl-3-dichlorovinyl-cyclopropanecarboxylic acid tetrafluoro-3-chlorobenzyl ester, 2,2-dimethyl-3-dichlorovinyl-cyclopropanecarboxylic acid 2,3,6-trifluorobenzyl ester, 2,2-dimethyl-3-dichlorovinyl-cyclopropanecarboxylic acid trifluoro-3,5-dichlorobenzyl ester, 2,2-dimethyl-3-dichlorovinyl-cyclopropanecarboxylic acid 2,6-difluoro-3,5-dichlorobenzyl ester, 2,2-dimethyl-3-dichlorovinyl-cyclopropanecarboxylic acid 2,3-difluoro-5-chlorobenzyl ester, 2,2-dimethyl-3-dichlorovinyl-cyclopropanecarboxylic acid 2-fluoro-3,5-dichlorobenzyl ester, and the corresponding 3-dibromovinyl compounds.

The esters listed imply both the racemic and the optically active isomers as well as the cis- and/or trans-isomers.

The present invention also provides a process for the preparation of an ester (I) in which (a) a compound of the general formula

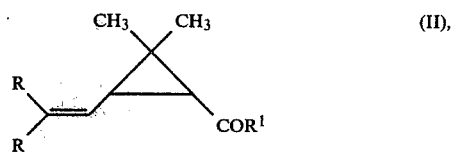

in which
R has the meaning stated above, and
R$^1$ represents halogen, OH or C$_{1-4}$-alkoxy,
is reacted with a compound of the general formula

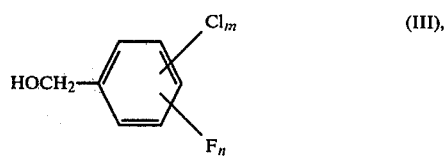

in which
m and n have the meanings stated above,
at a temperature between 20° and 120° C., optionally in the presence of an inert diluent (which term includes a solvent), or (b) a salt of the general formula

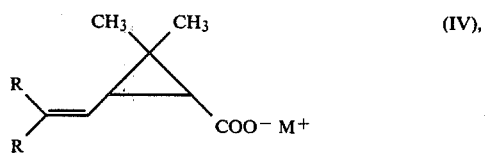

in which
R has the meaning stated above and
M$^+$ denotes an alkali metal cation, an equivalent of an alkaline earth metal cation or a primary, secondary or tertiary ammonium ion,
is reacted with a compound of the general formula

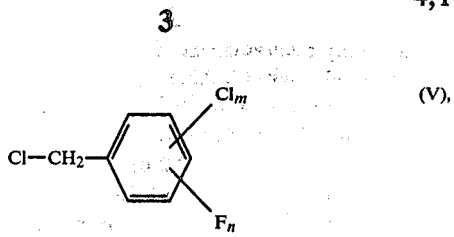 (V), in which m and n have the meanings stated above, in a polar solvent, at a temperature between 20° and 100° C., or (c) a compound of the general formula

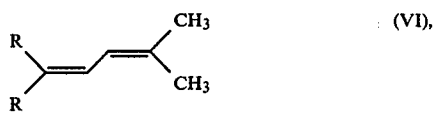 (VI), in which

R has the meaning stated above, is reacted with a compound of the general formula

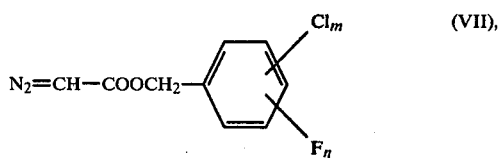 (VII), in which m and n have the meanings stated above, at a temperature between 50° and 120° C., in the presence of copper or a copper compound.

The compounds of the formula (I) exist in several stereoisomers. The substituents on the cyclopropane ring can be in the cis- or trans-position to one another. The carbon atoms $C_1$ and $C_3$ can in each case have either the R-configuration or the S-configuration and thus lead to optically active or racemic cis- and/or trans-isomers.

If 2,2-dimethyl-3-dichlorovinylcyclopropanecarboxylic acid chloride is used as the compound of the formula (II) and pentafluorobenzyl alcohol as the benzyl alcohol of the formula (III), the course of the reaction for process variant (a) can be represented by the following equation:

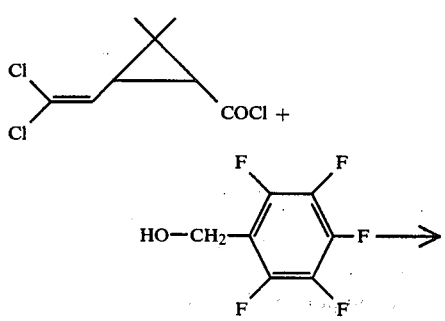

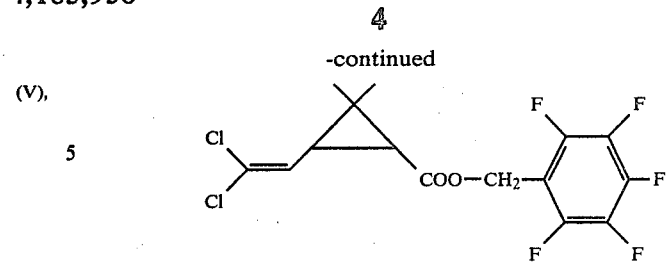

The compounds of the general formula (II) are known (German Offenlegungsschrift (German Published Specification) No. 2,439,177).

Alcohols of the general formula (III) are known (J. Chem. Soc. C, 1967, 293; J. Chem. Soc. 1962, 3227; J. Chem. Soc. 1961, 808; J. Chem. Soc. 1959, 166; and J. Med. Chem. 11, 814 (1968) and can be prepared, for example, by reducing the corresponding carbonyl compounds of the general formula

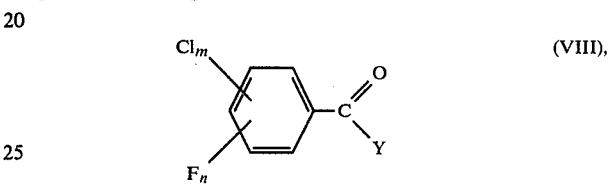 (VIII), in which m and n have the meanings stated above and

Y represents hydroxyl, alkoxy, chlorine, fluorine or hydrogen, with complex metal hydrides.

If an excess of LiAlH$_4$ is used, it is possible during this process simultaneously to remove one or two fluorine atoms reductively from the nucleus.

Carbonyl compounds of the formula (VIII) which are required for the reduction are known and can be prepared in a known manner (Synthesis 1976, page 652).

When 2,4,6-trifluorobenzaldehyde is used, the reduction of the aldehydes or acid halides of the formula (VIII) can be represented by the following equation:

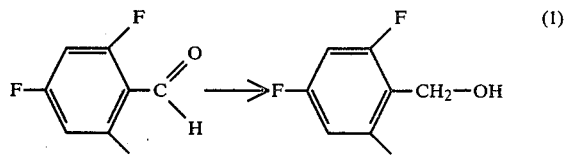 (1)

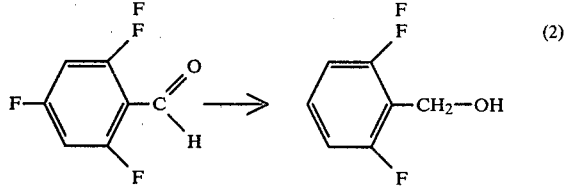 (2)

Equation (1) shows the reduction of the carbonyl function which is carried out using metal hydrides such as NaBH$_4$ or LiAlH$_4$. The reduction is carried out in the presence of inert organic diluents, at temperatures of from 0° to 100° C.

In addition to inert organic diluents, such as ethers (for example diethyl ether, dioxane or THF), alcohols (for example ethyl alcohol or methyl alcohol) or mixtures thereof with water, water is also a suitable diluent for carrying out the reduction with NaBH$_4$.

Aprotic, inert organic diluents, such as ethers (for example diethyl ether, dioxane or THF), are suitable diluents for carrying out the reduction with other complex metal hydrides, such as LiAlH$_4$.

The compounds of the general formula (VIII) which are to be reduced are, in general, dissolved in one of the diluents mentioned and the reducing agent is added. It is also possible, however, to add the reducing agent to the compounds to be reduced at lower temperatures (−30° to −50° C.) in a solvent and to initiate the reduction and to allow it to take place by raising the temperature slowly (if appropriate up to 50°–60° C.).

The reaction is customarily carried out at normal pressure.

If appropriate, the reaction mixture is worked up by adding to it a quantity of water corresponding to the reducing agent employed and subsequently distilling the organic phase.

When LiAlH$_4$ is used, if it is intended to reduce only the carbonyl function, only the stoichiometric quantity of LiAlH$_4$ required for this purpose may be used. When metal hydrides with a more gentle reducing action are used as the reducing agent, an excess of metal hydride is of no consequence for the course of the reaction.

Equation (2) shows the reduction of the carbonyl function when a fluorine substituent at the p-position in the nucleus is simultaneously removed reductively. It is necessary to use LiAlH$_4$ or hydride-donating agents of a greater reducing power than NaBH$_4$ as the reducing agent for this reaction. In addition to the quantity required for the reduction of the carbonyl function, one reduction equivalent of LiAlH$_4$ is required here for each fluorine substituent which is to be removed.

Ethers, especially THF, have proved particularly suitable as diluents.

The reduction with LiAlH$_4$ is carried out at temperatures between 20° and 100° C., preferably between 50° and 70° C. The reaction is carried out and the products are worked up as mentioned above.

The following may be mentioned as examples of compounds of the formula (III): pentafluorobenzyl alcohol, 2,3,5,6-tetrafluorobenzyl alcohol, 2,4,6-trifluorobenzyl alcohol, 2,3,5-trifluorobenzyl alcohol, 1,4-difluorobenzyl alcohol, 3,5-difluorobenzyl alcohol, 2,6-difluorobenzyl alcohol, tetrafluoro-3-chlorobenzyl alcohol, 2,4,6-trifluoro-3,5-dichlorobenzyl alcohol, 2,6-difluoro-3,5-dichlorobenzyl alcohol, 2,3-difluoro-5-chlorobenzyl alcohol and 2-fluoro-3,5-dichlorobenzyl alcohol.

If R represents fluorine or bromine, then the following benzyl alcohols are also preferred: pentachlorobenzyl alcohol, 2,3,5,6-tetrachlorobenzyl alcohol, 2,3,4,5-tetrachlorobenzyl alcohol, 2,3,4,6-tetrachlorobenzyl alcohol, 2,3,5-trichlorobenzyl alcohol, 2,4,5-trichlorobenzyl alcohol, 3,5-dichlorobenzyl alcohol, 2,4-dichlorobenzyl alcohol and 2,6-dichlorobenzyl alcohol.

A number of the benzyl alcohols of the general formula (III) are new. The new compounds can be defined by the general formula

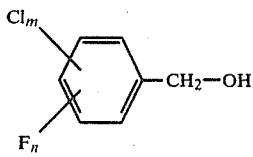

(III), wherein
 m represents 0, 1 or 2 and
 n represents 1, 2, 3 or 4, and if m represents 0 and n represents 2, position 6 of the phenyl ring must be unsubstituted.

The new benzyl alcohols from the group 2,3,5,6-tetrafluorobenzyl alcohol, 2,4,6-trifluorobenzyl alcohol, 2,3,5-trifluorobenzyl alcohol, 2,4-difluorobenzyl alcohol, 3,5-difluorobenzyl alcohol, tetrafluoro-3-chlorobenzyl alcohol, 2,4,6-trifluoro-3,5-dichlorobenzyl alcohol, 2,6-difluoro-3,5-dichlorobenzyl alcohol, 2,3-difluoro-5-chlorobenzyl alcohol and 2-fluoro-3,5-dichlorobenzyl alcohol are particularly preferred.

If sodium 2,2-dimethyl-3-dichlorovinylcyclopropane-1-carboxylate is used as the salt of the general formula (IV) and pentafluorobenzyl chloride is used as the benzyl chloride of the general formula (V), the course of the reaction can be represented for process variant (b) by the following equation:

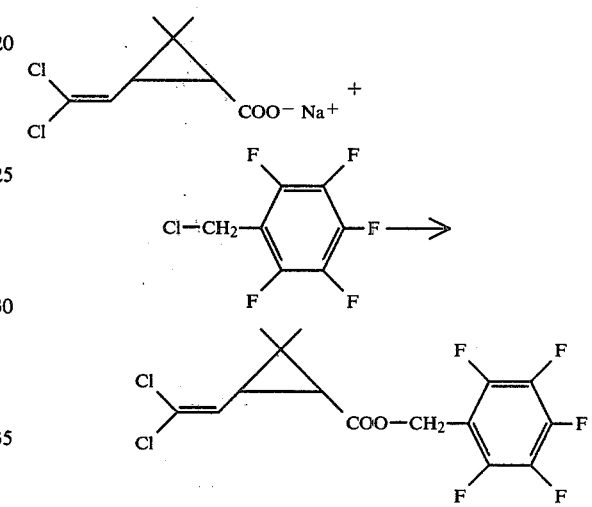

The salts of the formula (IV) which can be used as starting materials in carrying out process variant (b) are known (DOS (German Published Specification) No. 2,436,178). Benzyl halides of the formula (V) which are also required as reactants are known (J. Chem. Soc. 1962, 3227) and can be prepared by halogenating the corresponding toluenes or by reacting the corresponding benzyl alcohols of the formula (III) with chlorinating agents such as SOCl$_2$. Pentafluorobenzyl chloride may be mentioned as an example of the benzyl halides (V) which can be used according to the invention.

Process variant (b) is carried out in polar organic diluents, such as ketones (for example acetone), nitriles (for example acetonitrile), acid amides (for example DMF or hexamethylphosphoric acid triamide) or mixtures thereof with water. The process is carried out at temperatures between 20° and 100° C.

The process may be carried out in the presence or absence of suitable catalysts. Suitable catalysts are peralkylated polyamines (for example tetramethylethylenediamine).

The reaction may be carried out as described in Synthesis 1975, page 805.

If 1,1-dichloro-4-methyl-1,3-pentadiene is used as the compound of the general formula (VI) and diazoacetic acid pentafluorobenzyl ester is used as the compound of the formula (VII), the course of the reaction can be represented for process variant (c) by the following equation:

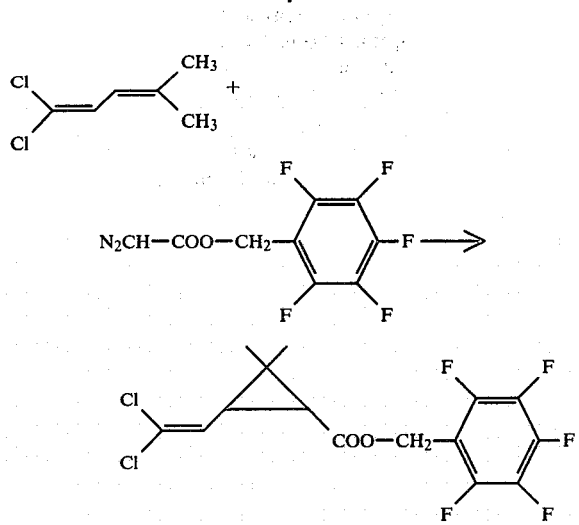

The compounds of the general formula (VI) to be used as starting compounds in process variant (c) are known (Coll. Czech. Chem. Comm. 24, 2230 (1959)). Compounds of the general formula (VII) are new. They can be obtained, in a manner which is in itself known, by converting the benzyl alcohols of the general formula (III) into their corresponding diazoacetic acid esters. This is achieved by diazotizing with sodium nitrite, in a manner which is in itself known, the hydrochlorides of the corresponding glycine esters (see German Offenlegungsschrift (German Published Specification) No. 2,400,188).

The glycine esters used for this purpose can be prepared by reacting glycine, in a manner which is in itself known (J. Am. Chem. Soc. 91, 1135 (1969)), with the benzyl alcohols of the general formula (III) in the presence of an anhydrous acid, preferably hydrogen chloride, and isolating the glycine ester salts by precipitation with ether or with a solvent in which the products are not soluble but in which the starting materials are soluble.

The glycine esters can also be obtained by reducing azidoacetic acid esters of the general formula

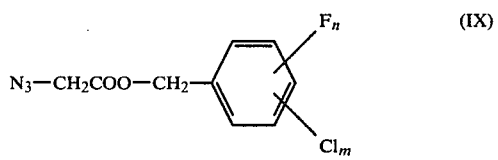

in which
m and n have the meanings stated above,
with catalytically activated hydrogen or with another reducing agent, as has been disclosed in Ann. 498, page 50 (1932) and Houben-Weyl, Methoden der organischen Chemie (Methods of Organic Chemistry), Volume XI/2, page 354.

The azido-esters of the formula (IX) may be obtained, in a manner which is in itself known, by reacting sodium azide with chloroacetic acid esters of the general formula

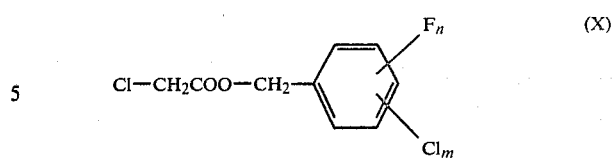

in which
n and m have the meanings stated above,
in a polar organic solvent (Soc. 93, page 669, (1908)).

The olefin of the formula (VI) is generally employed in at least a two-fold, preferably a 10–20-fold, excess. The reaction to give the compounds of the formula (I) according to the invention is accomplished by adding compounds of the formula (VII), appropriately in the form of a mixture with an olefin of the formula (VI), dropwise, at temperatures between 50° and 150° C., to a suspension of copper or a compound thereof (or another heavy metal compound) and the olefin of the formula (VI). The commencement of the reaction is indicated by the elimination of nitrogen. The products are obtained by separation by means of distillation. The olefin which has been employed in excess and is produced in the course of the distillation can be recycled again into the reaction zone together with fresh diazo-ester in a continuous mode of reaction.

As already mentioned, the compounds according to the present invention are distinguished by an excellent insecticidal and acaricidal activity. They are therefore active against plant pests, pests harmful to health and pests of stored products and combine a low phytotoxicity with a good action against sucking and biting insects and against mites.

For this reason, the compounds according to the invention can be employed successfully as pesticides in plant protection and in the hygiene field and the field of protection of stored products.

The active compounds are well tolerated by plants, have a favorable level of toxicity to warm-blooded animals, and can be used for combating arthropod pests, especially insects and arachnids which are encountered in agriculture, in forestry, in the protection of stored products and of materials, and in the hygiene field. They are active against normally sensitive and resistant species and against all or some stages of development. The abovementioned pests include:

from the class of the Isopoda, for example, *Oniscus asellus, Armadillidium vulgare* and *Porcellio scaber;* from the class of the Diplopoda, for example *Blaniulus guttulatus;* from the class of the Chilopoda, for example *Geophilus carpophagus* and *Scutigera* spec.;

from the class of the Symphyla, for example *Scutigerella immaculata;* from the order of the Thysanura, for example *Lepisma saccharina;* from the order of the Collembola, for example *Onychiurus armatus;* from the order of the Orthoptera, for example *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria;* from the order of the Dermaptera, for example *Forficula auricularia;* from the order of the Isoptera, for example *Reticulitermes* spp.;

from the order of the Anoplura, for example *Phylloxera vastatrix*, *Pemphigus* spp., *Pediculus humanus corporis*, *Haematopinus* spp. and *Linognathus* spp.;

from the order of the Mallophaga, for example *Trichodectes* spp. and *Damalinea* spp.;

from the order of the Thysanoptera, for example *Hercinothrips femoralis* and *Thrips tabaci*;

from the order of the Heteroptera, for example *Eurygaster* spp., *Dysdercus intermedius*, *Piesma quadrata*, *Cimex lectularius*, *Rhodnius prolixus* and *Triatoma* spp.;

from the order of the Homoptera, for example *Aleurodes brassicae*, *Bemisia tabaci*, *Trialeurodes vaporariorum*, *Aphis gossypii*, *Brevicoryne brassicae*, *Cryptomyzus ribis*, *Doralis fabae*, *Doralis pomi*, *Eriosoma lanigerum*, *Hyalopterus arundinis*, *Macrosiphum avenae*, *Myzus* spp., *Phorodon humuli*, *Rhopalosiphum padi*, *Empoasca* spp., *Euscelis bilobatus*, *Nephotettix cincticeps*, *Lecanium corni*, *Saissetia oleae*, *Laodelphax striatellus*, *Nilaparvata lugens*, *Aonidiella aurantii*, *Aspidiotus hederae*, *Pseudococcus* spp. and *Psylla* spp.;

from the order of the Lepidoptera, for example *Pectinophora gossypiella*, *Bupalus piniarius*, *Cheimatobia brumata*, *Lithocolletis blancardella*, *Hyponomeuta padella*, *Plutella maculipennis*, *Malacosoma neustria*, *Euproctis chrysorrhoea*, *Lymantria* spp., *Bucculatrix thurberiella*, *Phyllocnistis citrella*, *Agrotis* spp., *Euxoa* spp., *Feltia* spp., *Earias insulana*, *Heliothis* spp., *Laphygma exigua*, *Mamestra brassicae*, *Panolis flammea*, *Prodenia litura*, *Spodoptera* spp., *Trichoplusia ni*, *Carpocapsa pomonella*, *Pieris* spp., *Chilo* spp., *Pyrausta nubilalis*, *Ephestia kuehniella*, *Galleria mellonella*, *Cacoecia podana*, *Capua reticulana*, *Choristoneura fumiferana*, *Clysia ambiguella*, *Homona magnanima* and *Tortrix viridana*;

from the order of the Coleoptera, for example *Anobium punctatum*, *Rhizopertha dominica*, *Bruchidius obtectus*, *Acanthoscelides obtectus*, *Hylotrupes bajulus*, *Agelastica alni*, *Leptinotarsa decemlineata*, *Phaedon cochleariae*, *Diabrotica* spp., *Psylliodes chrysocephala*, *Epilachna varivestis*, *Atomaria* spp., *Oryzaephilus surinamensis*, *Anthonomus* spp., *Sitophilus* spp., *Otiorrhynchus sulcatus*, *Cosmopolites sordidus*, *Ceuthorrhynchus assimilis*, *Hypera postica*, *Dermestes* spp., *Trogoderma* spp., *Anthrenus* spp., *Attagenus* spp., *Lyctus* spp., *Meligethes aeneus*, *Ptinus* spp., *Niptus hololeucus*, *Gibbium psylloides*, *Tribolium* spp., *Tenebrio molitor*, *Agriotes* spp., *Conoderus* spp., *Melolontha melolontha*, *Amphimallon solstitialis* and *Costelytra zealandica*;

from the order of the Hymenoptera, for example *Diprion* spp., *Hoplocampa* spp., *Lasius* spp., *Monomorium pharaonis* and *Vespa* spp.;

from the order of the Diptera, for example *Aedes* spp., *Anopheles* spp., *Culex* spp., *Drosophila melanogaster*, *Musca* spp., *Fannia* spp., *Calliphora erythrocephala*, *Lucilia* spp., *Chrysomyia* spp., *Cuterebra* spp., *Gastrophilus* spp., *Hyppobosca* spp., *Stomoxys* spp., *Oestrus* spp., *Hypoderma* spp., *Tabanus* spp., *Tannia* spp., *Bibio hortulanus*, *Oscinella frit*, *Phorbia* spp., *Pegomyia hyoscyami*, *Ceratitis capitata*, *Dacus oleae* and *Tipula paludosa*;

from the order of the Siphonaptera, for example *Xenopsylla cheopis* and *Ceratophyllus* spp.;

from the class of the Arachnida, for example *Scorpio maurus* and *Latrodectus mactans*;

from the order of the Acarina, for example *Acarus siro*, *Argas* spp., *Ornithodoros* spp., *Dermanyssus gallinae*, *Eriophyes ribis*, *Phyllocoptruta oleivora*, *Boophilus* spp., *Rhipicephalus* spp., *Amblyomma* spp., *Hyalomma* spp., *Ixodes* spp., *Psoroptes* spp., *Chorioptes* spp., *Sarcoptes* spp., *Tarsonemus* spp., *Bryobia praetiosa*, *Panonychus* spp. and *Tetranychus* spp..

When used against hygiene pests and pests of stored products, the active compounds are distinguished by an excellent residual activity on wood and clay as well as a good stability to alkali on limed substrates.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances and in coating compositions, for use on seed, and formulations used with burning equipment, such as fumigating cartridges, fumigating cans, fumigating coils and the like, as well as ULV cold mist and warm mist formulations.

These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as halogenated hydrocarbons, e.g. dichlorodifluoromethane and trichloromethane, as well as butane, propane, nitrogen and carbon dioxide; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes, (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as solid carriers, ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules; crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

Such active compounds may be employed alone or in the form of mixtures with one another and/or with such solid and/or liquid dispersible carrier vehicles and/or with other known compatible active agents, especially plant protection agents, such as other arthorpodicides or nematicides, fungicides, bactericides, rodenticides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1-95% by weight, and preferably 0.5-90% by weight, of the mixture, whereas carrier composition mixtures suitable for direct application or field application generally contemplate those in which the active compound is present in an amount substantially between about 0.0000001-100, preferably 0.01-10%, by weight of the mixture. Thus, the present invention contemplates overall compositions which comprise mixtures of a conventional dispersible carrier such as (1) a dispersible inert finely divided carrier solid, and/or (2) a dispersible carrier liquid such as an inert organic solvent and/or water, preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001-95%, and preferably 0.01-95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50-100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20-100% by weight of the active compound.

Furthermore, the present invention contemplates methods of selectively killing, combating or controlling pests, e.g. arthropods, which comprises applying to at least one of correspondingly (a) such arthropods, and (b) the corresponding habitat thereof, i.e. the locus to be protected, e.g. to a growing crop, to an area where a crop is to be grown or to a domestic animal, a correspondingly combative or toxic amount, i.e. an arthropodicidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, dry dressing, moist dressing, wet dressing, slurry dressing, encrusting, and the like.

It will be realized, of course, that the concentration of the particular active compound utilized in admixture with the carrier vehicle will depend upon the intended application. Therefore, in special cases it is possible to go above or below the aforementioned concentration ranges.

The process of the present invention is illustrated by the following preparative examples:

EXAMPLE 1

Examples of the preparation of polyfluorobenzyl alcohols:

(a) Reduction of polyfluorobenzoyl fluorides while preserving the nuclear substitution.

0.1 mole of the particular polyfluorobenzoyl fluoride and 0.08 mole of sodium borohydride in 80 ml of absolute dioxane were warmed for 5 hours at 50° while stirring vigorously. The mixture was then poured into water and extracted with ether in order to obtain therefrom, in 95% yield, the desired alcohol as a colorless oil having an unchanged halogen content in the aromatic nucleus.

It was possible, for example, in this way to prepare and to characterize by spectroscopic data, the following:

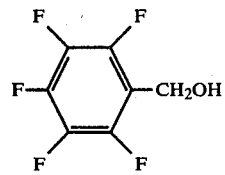

IR (cm$^{-1}$): 3,400, 2,900, 1,670, 1,510, 1,310, 1,300, 1,220, 1,120, 1,050, 1,030, 950, 930, 870.

NMR, CDCl$_3$ (ppm): 4.7 s (2), 2.4 s (1).

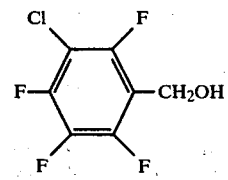

IR (cm$^{-1}$): 3,300, 1,650, 1,490, 1,380, 1,280, 1,230, 1,130, 1,090, 1,030, 1,000, 930, 860, 750.

NMR: 4.7 s (2), 2.8 s (1).

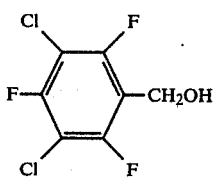

NMR (ppm) CDCl$_3$: 4.7 s (2) 2.6 s (1).
mass spectrum m/e: 230 (M).

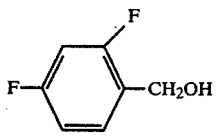

IR (cm$^{-1}$): 3,300, 2,900, 1,620, 1,510, 1,430, 1,280, 1,230, 1,140, 1,100, 1,040, 1,010, 960, 860, 820.
NMR: 6.5–7.5 m (3), 4.6 s (2), 3.0 s (1).

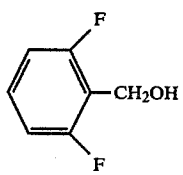

IR (cm$^{-1}$): 3,300, 2,950, 2,870, 1,630, 1,600, 1,470, 1,380, 1,270, 1,220, 1,200, 1,190, 1,110, 1,020, 910, 930, 790.
NMR: 6.7–7.5 m (3), 4.7 s (2), 3.2 s (1).
The compounds of the formulae

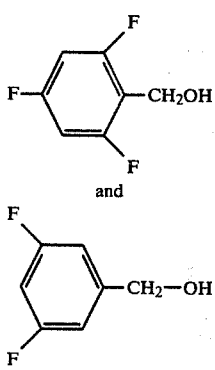

were also obtained analogously.

(b) Reduction of polyfluorobenzoic acid fluorides while modifying the nuclear substitution 0.01 mole of the particular polyfluorobenzoyl fluoride and 0.0075 mole of LiAlH$_4$ in 80 ml of absolute THF were boiled for 5 hours. After using rather more than the calculated quantity of water for decomposition, the hydroxide precipitate was filtered off and the benzyl alcohol which had been defluorinated in the p-position was isolated in 80–90% yield. The following could be prepared in this way:

Starting compound        Benzyl alcohol

-continued

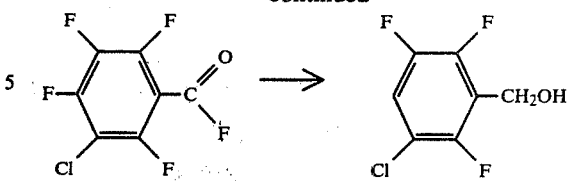

NMR (CDCl$_3$), ppm: 7 m (1), 4.65 (2), 3.3 (1).
mass spectrum (m/e) 196, 75, 142, 147, 161, 167, 178, 113, 98, 71.

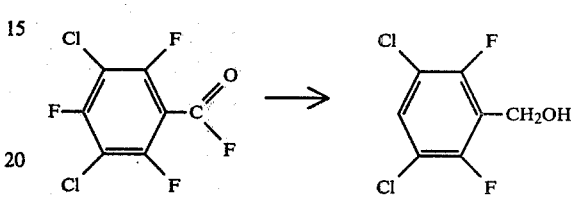

NMR (CDCl$_3$), ppm: 7.2 (1), 4.6 (2), 2.9 (1).

In an alternative procedure, 0.01 mole of the polyfluorobenzoyl fluoride and 0.12 mol of LiAlH$_4$ in 100 ml of absolute THF were boiled for 5 hours. The benzyl alcohol which had been defluorinated in the o-position and the p-position was isolated by working up as above.

The following could be prepared in this way:

Starting compound        Benzyl alcohol

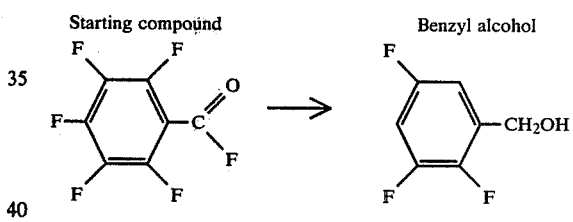

NMR (CDCl), ppm 7 m (2) S, 4.6 (2) S 2.8 (1).

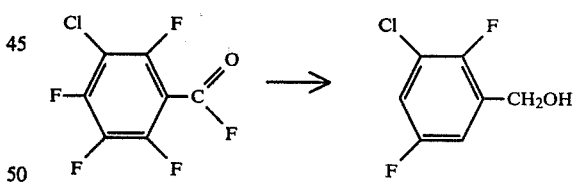

mass spectrum (m/e): 178, 113, 115, 143, 148, 161, 129, 125.

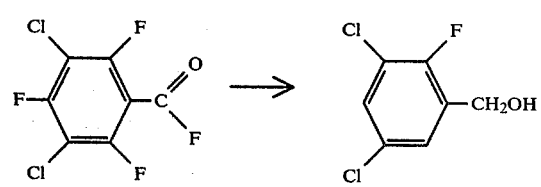

NMR (CDCl$_2$) (ppm) 7.2 m (2), 4.7 (2), S 2.8 (1).

EXAMPLE 2

(a) 2,2-Dimethyl-3-dichlorovinyl-cyclopropanecarboxylic acid pentafluorobenzyl ester

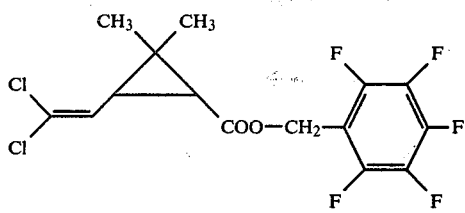
(1)

0.1 mole of 2,2-dimethyl-3-dichlorovinyl-cyclopropanecarboxylic acid chloride (cis/trans) was added dropwise at 70° C. to 0.1 mole of pentafluorobenzyl alcohol. The mixture was then heated at 120° C. for a few minutes until gas evolution ceased. The yield of an oil, which was pure by thin-layer chromatography, was quantitative. b.p.$_{0.1}$ 120°–130° C.

Spectroscopic data:

IR (cm$^{-1}$): 2,900, 1,740, 1,660, 1,510, 1,460, 1,415, 1,385, 1,355, 1,310, 1,220, 1,161, 1,130, 1,080, 1,050, 995, 970, 940, 810, 780.

mass spectrum (m/e): 181, 163, 165, 91, 127, 109, 191, 207, 353, 388 (M).

NMR (ppm): 6.6 and 5.6 d (1), 5.2 s (2), 0.8–2.4 m (8). After standing for several days colorless crystals deposited, m.p. 74° C., which turned out to be the cis-isomer.

Other esters of the same acid, which are characterized by the spectroscopic data given below, could be prepared in the same way:

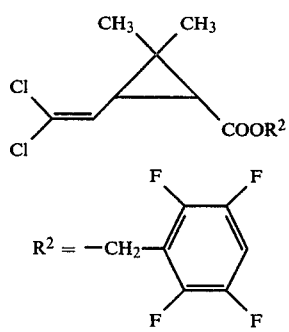
(2)

IR (cm$^{-1}$): 1,730, 1,630.
mass spectrum (m/e): 763, 91, 127, 207, 335, 370 (M).
NMR (ppm): 7 (1); 6.2, 5.6 d (1); 5.2 s (2); 0.9–2.5 m (8).

$R^2 = -CH_2-$ (with 2,4,5-trifluorophenyl) (3)

IR (cm$^{-1}$): 1,730, 1,630.
mass spectrum (m/e): 145, 163, 165, 129, 191, 317, 352 (M).
NMR (ppm): 7 m (2); 6.2; 5.6 d (1); 5.1 s (2), 0.9–2.5 m (8).

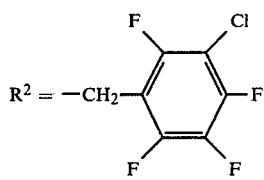
(4)

IR (cm$^{-1}$): 2,950, 1,740, 1,650, 1,630, 1,500, 1,420, 1,390, 1,350, 1,280, 1,230, 1,160, 1,135, 1,100, 1,020, 940, 870, 820, 780.

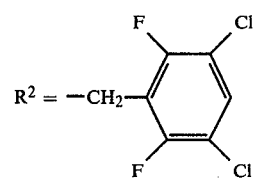
(5)

IR (cm$^{-1}$): 1,735, 1,630.
mass spectrum (m/e): 195, 163, 165, 127, 91, 191, 207, 367, 402 (M).

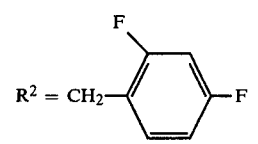
(6)

IR (cm$^{-1}$): 2,950, 1,735, 1,620, 1,515, 1,460, 1,350, 1,280, 1,230, 1,160, 1,140, 1,100, 1,090, 1,055, 990, 965, 920, 885, 850, 820.

mass spectrum (m/e): 127, 109, 163, 165, 91, 191, 207, 251, 299, (M-Cl).

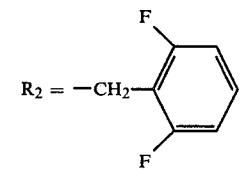
(7)

IR (cm$^{-1}$): 2,950, 1,735, 1,635, 1,600, 1,485, 1,280, 1,230, 1,170, 1,140, 1,120, 1,055, 920.

mass spectrum (m/e): 127, 109, 163, 165, 91, 191, 207, 251, 299, 334 (M).

NMR (ppm): 6.7–7.6 m (3), 6.2 and 5.6 d (1); 5.2 s (2), 0.7–2.4 m (8).

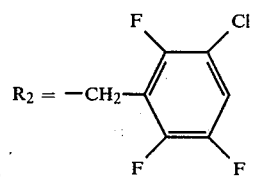
(8)

IR (cm$^{-1}$): 1,730, 1,620.
mass spectrum (m/e): 163, 165, 179, 127, 91, 191, 207, 351, 386 (M).

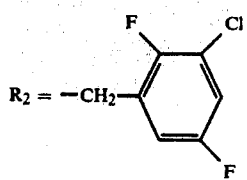
(9)

IR (cm⁻¹): 1,730, 1,620.

mass spectrum (m/e): 161, 163, 165, 91, 191, 207, 333, 368 (M).

(b) The following compounds were obtained by analogous methods:

| Example No. | Formula |
|---|---|
| 10. | 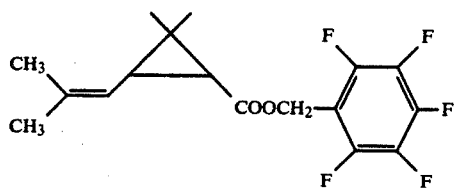 |
| 11. | 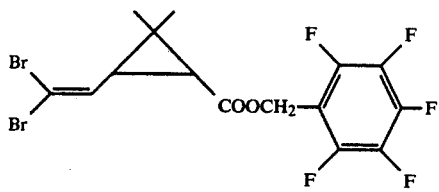 |
| 12. | 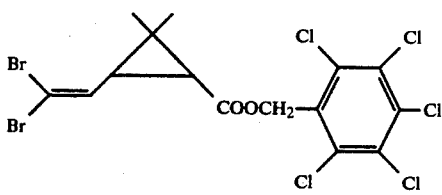 |
| 13. | 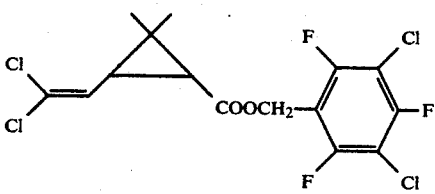 |
| 14. | 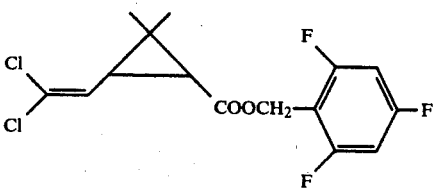 |
| 15. | 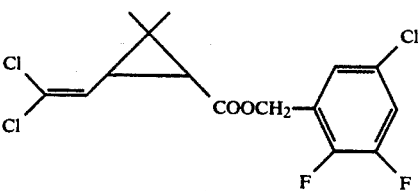 |

EXAMPLE 3

(±) trans-2,2-Dimethyl-3-dichlorovinyl-cyclopropanecarboxylic acid pentafluorobenzyl ester 0.1 mole of potassium (±) trans-2,2-dimethyl-3-dichlorovinyl-cyclopropanecarboxylate and 0.1 mole of pentafluorobenzyl chloride were heated in acetonitrile until the reaction was complete. After concentrating, taking up in water/petroleum ether and concentrating the organic phase, a colorless oil was obtained, in the NMR spectrum of which the doublet mentioned in Example 2 for the vinyl proton of the cis-ester was lacking.

The insecticidal activity of the compounds of this invention is illustrated by the following biotest examples in which the compounds according to the present invention are each identified by the number (given in brackets) from the preparative examples hereinabove:

EXAMPLE 4

Aerosol Test

Test insect: *Musca domestica* (phosphoric acid ester resistant)
Solvent: Acetone To produce a suitable preparation of active compound, the active compound was dissolved in the desired amount of acetone.

A wire cage containing 25 test animals was suspended in the middle of a gas-tight glass chamber of size 1 m³. When the chamber had again been closed, 2 ml of the active compound preparations were atomized therein. The condition of the test insects was constantly checked from outside, through the glass walls, and the time required for 100% destruction of the insects was determined.

The active compounds, amounts of active compound applied and times at which 100% destruction was achieved can be seen from the following table:

Table 1

| Active compounds | Aerosol Test (*Musca domestica*, resistant) Amount of active compound applied in 2 ml of acetone/ m³, in mg | LT₁₀₀ |
|---|---|---|
| (1) | 1 | 55' |
| (2) + (3) (1:1) | 15 | 55' |
| (4) | 5 | 25' |
| (7) | 15 | 60' = 47% |
| (16) | 1 | 36' |

EXAMPLE 5

Laphygma Test

Solvent: 3 parts by weight of dimethylformamide
Emulsifier: 1 part by weight of alkylaryl polyglycol ether To produce a suitable preparation of active compound, 1 part by weight of the active compound was mixed with the stated amount of solvent and the stated amount of emulsifier and the concentrate was diluted with water to the desired concentration.

Cotton leaves (*Gossypium hirsutum*) were sprayed with the preparation of the active compound until dewmoist and were then infested with caterpillars of the owlet moth (*Laphygma exigua*).

After the specified periods of time, the destruction in % was determined. 100% meant that all of the caterpillars had been killed whereas 0% indicated that none of the caterpillars had been killed.

The active compounds, the concentrations of the active compounds, the evaluation times and the results can be seen from the following table:

Table 2

| Active compounds | (insects which damage plants) Laphygma test | |
|---|---|---|
| | Active compound concentration in % | Degree of destruction in % after 3 days |
| (4) | 0.1 | 100 |
| | 0.01 | 100 |
| (1) | 0.1 | 100 |
| | 0.01 | 100 |
| (16) | 0.1 | 100 |
| | 0.01 | 100 |
| (8) + (15) (1:1) | 0.1 | 100 |
| | 0.01 | 100 |
| | 0.0001 | 90 |
| (2) + (3) (1:1) | 0.1 | 100 |
| | 0.01 | 100 |
| | 0.001 | 100 |

It will be appreciated that the instant specification and examples are set forth by way of illustration and not limitation, and that various modifications and changes may be made without departing from the spirit and scope of the present invention.

What is claimed is:

1. A 2,2-dimethyl-3-vinyl-cyclopropane carboxylic acid ester of a halogenated benzyl alcohol of the formula

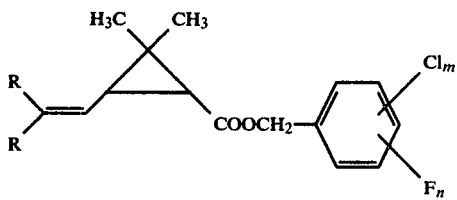

in which
each R independently represents F, Cl or Br
and m and n each independently represent 0, 1, 2, 3, 4 or 5 subject to the sum of m+n being not more than 5,
with the provisos that
(i) when each R represents F or Br then m and n cannot both be O, and
(ii) when each R represents Cl, then m represents 0, 1, 2, 3 or 4 and n represents 1, 2, 3, 4 or 5.

2. An ester according to claim 1, in which m is an integer from 2 to 5 and/or n is an integer from 3 to 5.

3. An ester according to claim 1, in which said ester is 2,2-dimethyl-3-dibromovinyl-cyclopropanecarboxylic acid pentafluorobenzyl ester of the formula

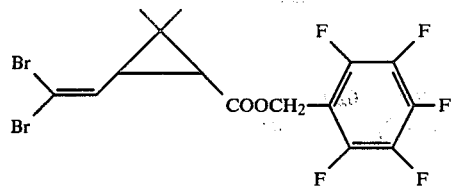

4. An ester according to claim 1, in which said ester is 2,2-dimethyl-3-dibromovinyl-cyclopropanecarboxylic acid pentachlorobenzyl ester of the formula

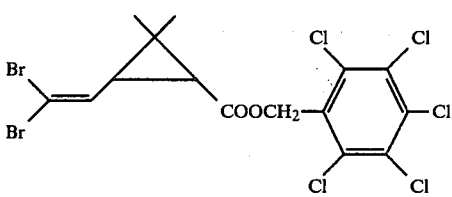

5. An ester according to claim 1, in which said ester is 2,2-dimethyl-3-dichlorovinyl-cyclopropanecarboxylic acid 2,4,6-trifluoro-3,5-dichlorobenzyl ester of the formula

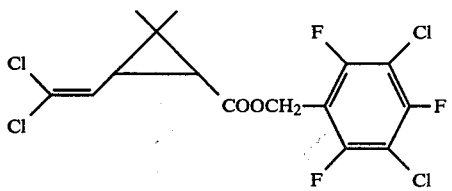

6. An arthropodicidal composition containing as active ingredient an arthropodicidally effective amount of an ester according to claim 1 in admixture with a diluent.

7. A method of combating arthropods which comprises applying to the arthropods, or to a habitat thereof, an arthropodicidally effective amount of an ester according to claim 1.

8. The method according to claim 7, in which said ester is
2,2-dimethyl-3-dibromovinyl-cyclopropanecarboxylic acid pentafluorobenzyl ester,
2,2-dimethyl-3-dibromovinyl-cyclopropanecarboxylic acid pentachlorobenzyl ester, or
2,2-dimethyl-3-dichlorovinyl-cyclopropanecarboxylic acid 2,4,6-trifluoro-3,5-dichlorobenzyl ester.

9. An ester according to claim 1 in the form of the cis-isomer.

* * * * *